(12) United States Patent
Groh et al.

(10) Patent No.: US 7,178,980 B2
(45) Date of Patent: Feb. 20, 2007

(54) X-RAY SYSTEM WITH OPERATING PARAMETERS THAT ARE AUTOMATICALLY SET DEPENDENT ON THE USE OF AUXILIARY EQUIPMENT

(75) Inventors: Burkhard Groh, Concord, CA (US); Volker Heer, Gundelsheim (DE); Mathias Hörnig, Erlangen (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 256 days.

(21) Appl. No.: 10/856,388

(22) Filed: May 28, 2004

(65) Prior Publication Data
US 2006/0153338 A1 Jul. 13, 2006

(30) Foreign Application Priority Data
May 30, 2003 (DE) ................. 103 24 905

(51) Int. Cl.
*G01D 18/00* (2006.01)
(52) U.S. Cl. .................................... 378/207
(58) Field of Classification Search ............... 378/95, 378/162, 207, 114, 115; 600/429
See application file for complete search history.

(56) References Cited

U.S. PATENT DOCUMENTS

| | | | | |
|---|---|---|---|---|
| 4,477,923 A | * | 10/1984 | Baumann et al. | 378/95 |
| 4,983,169 A | * | 1/1991 | Furukawa | 604/164.13 |
| 5,802,139 A | * | 9/1998 | Kusch et al. | 378/98 |
| 6,178,225 B1 | * | 1/2001 | Zur et al. | 378/98.2 |
| 6,324,254 B1 | | 11/2001 | Pflaum | |
| 6,778,628 B2 | * | 8/2004 | Yamazaki et al. | 378/8 |
| 2001/0050974 A1 | | 12/2001 | Schmitz | |

FOREIGN PATENT DOCUMENTS

DE 101 33 149 1/2003

* cited by examiner

*Primary Examiner*—Edward J. Glick
*Assistant Examiner*—Chih-Cheng Glen Kao
(74) *Attorney, Agent, or Firm*—Schiff Hardin LLP

(57) ABSTRACT

An x-ray system HAS adjustable operating parameters with a dependency existing between different auxiliary types of equipment selectable for an examination and a suitable setting of the parameter. A control system of the x-ray system has a data input device to detect the used auxiliary equipment, a data storage device with data concerning the relation between each type of auxiliary equipment and an optimal setting of the parameters therefor, and an adjustment device for automatically adjusting the parameter dependent on the selection of the auxiliary equipment.

9 Claims, 1 Drawing Sheet

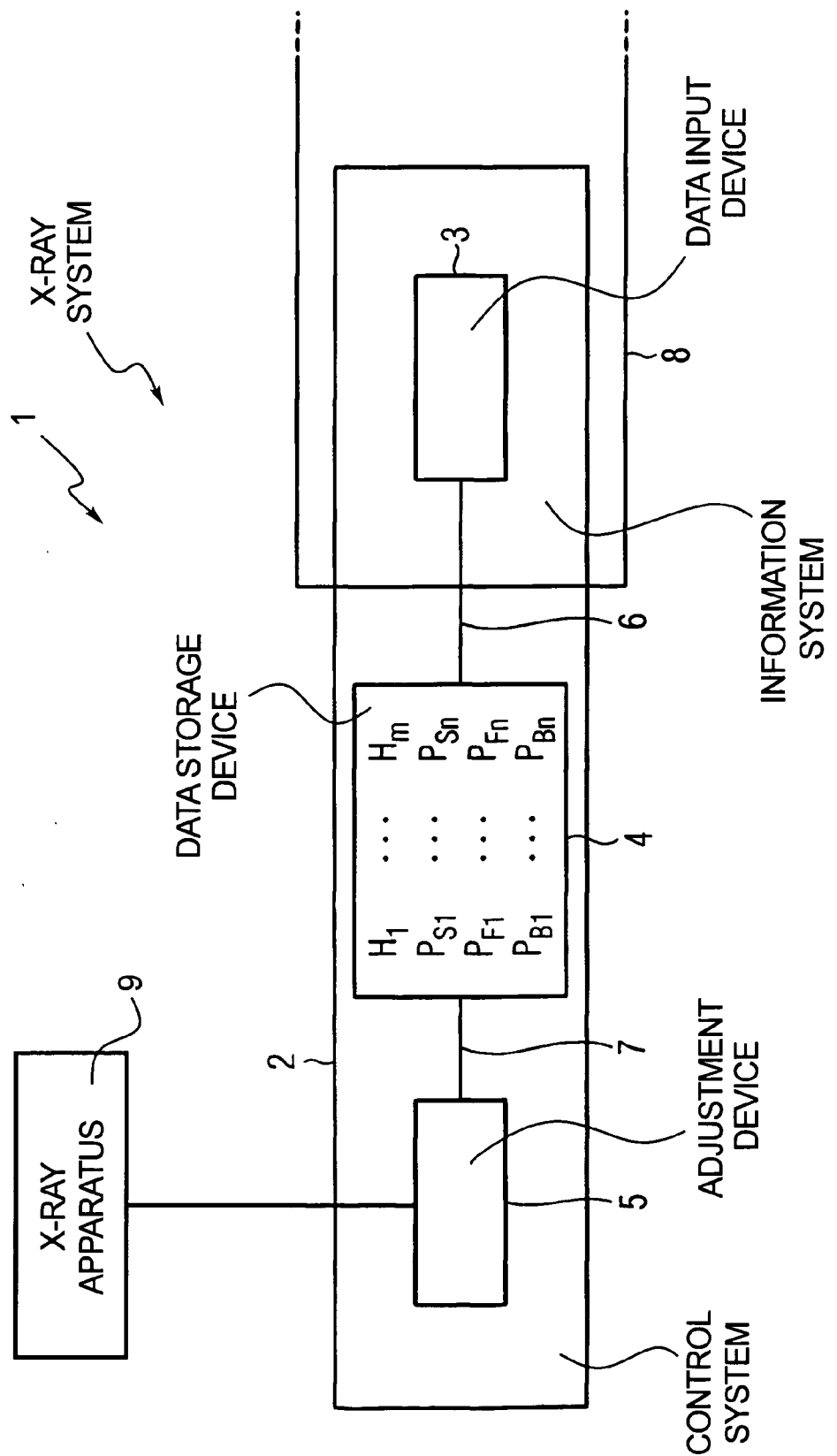

X-RAY SYSTEM WITH OPERATING PARAMETERS THAT ARE AUTOMATICALLY SET DEPENDENT ON THE USE OF AUXILIARY EQUIPMENT

BACKGROUND OF THE INVENTION

1. Field of the Invention

The present invention concerns an x-ray system of the type reusable with auxiliary equipment (for example, a contrast agent injector) to implement an examination. An x-ray system for medical-related applications, in which a contrast agent injector is used as auxiliary equipment, is known from German OS 198 53 964.

2. Description of the Prior Art

A medical-related x-ray system typically includes a number of adjustable apparatus parameters, with one optimal setting of the parameters exists for each examination to be implemented. The optimal setting of all of the apparatus parameters before each examination represents a very complicated and time-consuming procedure, such that it may not always take place in practice, and the functions and properties (in particular concerning the imaging quality) provided by the x-ray apparatus are only partially utilized.

In interventional procedures, it is customary to use auxiliary equipment (such as catheters and/or guide wires) which optimally should be exactly detectable in real time by x-ray transirradiation. From German OS 101 33 149, a vessel catheter is known having a design to ease the detection of the orientation of the catheter tip on an x-ray exposure. This requires a suitable correlation between the geometry and material properties of the catheter and the settings (for example, focus setting) of the x-ray apparatus. The finer the structures of the auxiliary equipment used in the examination, the greater the demands on the adjustment of the x-ray apparatus, and the time necessary for the adjustment is no longer available for the actual examination.

SUMMARY OF THE INVENTION

An object of the present invention is to provide for simple and time-saving operation of an x-ray system, with the optimal setting of at least one parameter of the x-ray system being dependent on the selection of auxiliary equipment for the x-ray examination.

This object is inventively by an x-ray system wherein auxiliary equipment which is either directly detectable by x-ray examination or at least influences the examination and/or image, is used for the implementation of an examination. The x-ray system has at least one adjustable parameter, and an optimal setting of the parameter is associated with each type of auxiliary equipment (for example, catheter, guide wire or contrast agent injector). The x-ray system has a control system with a data input device, a data storage device, and an adjustment device.

The data input device detects the auxiliary equipment currently used for the examination and preferably is a barcode scanner. A physical connection between the actual x-ray apparatus and the data input device is not necessarily present.

The data storage device contains data regarding the various auxiliary equipment which are relevant for use in connection with x-ray-related examinations, and contains data regarding the possible parameter settings of the x-ray apparatus. For example, by the adjustment of various parameters, the x-ray spectrum or the focus in the imaging process can be influenced or an image processing filter can be selected or adjusted. Furthermore, in the data storage device an association can exist between each auxiliary equipment or a combination of auxiliary equipment and the respective optimal setting of a parameter or a set of parameters therefor. The formation of this relation, for example, can ensue by explicit links in the databank, or the respective optimal parameter setting can be determined by calculation from properties of the auxiliary equipment.

The adjustment device is provided for automatic adjustment of the parameter or parameter set, dependent on the selection of the auxiliary equipment. Manual parameter setting by the operating personnel of the x-ray system thus is not necessary. The detection before the examination of the auxiliary equipment currently in use by data input device is sufficient for the adjustment of the x-ray apparatus coordinated with the respective auxiliary equipment.

In a preferred embodiment, the control system of the x-ray system is in communication with a medical information system which preferably includes an accounting (billing) system. The data identifying the auxiliary equipment, which are relevant both for charging for the examination and/or treatment with (cost unit) and for the selection of the parameters to be set in the examination (the data have both an economic and a technical information content), need to be detected only once before the use of the of the auxiliary equipment, preferably by means of a barcode scanner or another data acquisition device operating without physical contact. A databank having appropriate data stored therein is hereby accessed, which associates a set of operational, device-related and possible other data with each usable auxiliary equipment. An association between a specific x-ray-related system or a specific x-ray-related method and the type of the auxiliary equipment used for the examination is also provided at the same time in this manner, such that in practice supervision as to whether the selected auxiliary equipment is suitable or permitted for the respective system or the respective method can be implemented without additional effort.

An advantage of the invention is that, by giving a control system of an x-ray system with access to a database which provides (for each auxiliary equipment usable in the x-ray system) an optimal setting of the x-ray system, the full potential of the x-ray system can be utilized with extremely little effort and low probability of error.

DESCRIPTION OF THE DRAWINGS

The single FIGURE is a schematic block diagram of an x-ray system for medical-related applications in accordance with the invention.

DESCRIPTION OF THE PREFERRED EMBODIMENTS

The x-ray system 1 shown in the FIGURE has a control system 2 with a barcode scanner as a data input device 3, a data storage device 4 and an adjustment device 5. The individual devices 3, 4, 5 of the control system 2 need not necessarily be located in close spatial correlation, but they are in any case linked via data lines 6, 7. The data input device 3 is at the same time part of a medical information system 8 which includes an accounting system. By means of the adjustment device 5, an examination to be implemented with an x-ray apparatus 9, for example a computed tomography apparatus, can be influenced with regard to hardware and/or software.

The adjustment of the x-ray system 1 in the examination can be specified by one or more parameters, such as a parameter $P_S$ influencing the x-ray spectrum, a parameter $P_F$ influencing the focus in the imaging method, and a parameter $P_B$ influencing or adjusting an image processing filter. Each of the parameters $P_S$, $P_F$, $P_B$ can be set in the exemplary embodiment to n different values, such that each possible setting of the x-ray system 1 can be described by a triplet of parameters ($P_{Si}$, $P_{Fj}$, $P_{Bk}$) ($1 \leq i \leq n$; $1 \leq j \leq n$; $1 \leq k \leq n$). The number of the possible settings of the parameters $P_S$, $P_F$, $P_B$ is not necessarily identical for each of the parameters $P_S$, $P_F$, $P_B$. Moreover, continuous adjustment can be provided. Each of the parameters $P_{S1} \ldots P_{Sn}$, $P_{F1} \ldots P_{Fn}$, $P_{B1} \ldots P_{Bn}$ in principle also can be manually set or corrected; but this is not necessary in the x-ray system 1.

In an examination with the x-ray system 1, in the considered example a guide wired to be inserted into a blood vessel of a patient is provided as an auxiliary equipment H, for which m different variants are available, indicated by $H_1 \ldots H_M$. One optimal setting of the parameters $P_S$, $P_F$, $P_B$ is unambiguously associated with each of the m alternative useable guide wires H. These associations are stored in the data storage device 4. If a number of different types of auxiliary equipment $H_a$, $H_b$ ($1 \leq a \leq m$; $1 \leq b \leq m$) are simultaneously used in an examination, a suitable setting of the parameters $P_S$, $P_F$, $P_B$ is also respectively associated with such an auxiliary equipment combination.

The auxiliary equipment H used in the examination is typically a disposable (one-time use) article, the costs are to be calculated in connection with the examination and/or treatment. The disposable article H typically is enclosed in sterilized form in packaging having a barcode. Before the packaging is opened, the barcode is read with the barcode scanner 3 in order to identify the auxiliary equipment H provided for the examination. All associated data, both for the adjustment device 5 and for the information system 8, are already stored in the x-ray system 1. As a part of the information system 8, the data storage device 4 also can be spatially separate from the actual x-ray apparatus 9, which is adjusted by means of the adjustment device 5. The medical information system 8 preferably is part of a high-ranking hospital information system, or is identical with such. In addition to significant economization, the connection of the x-ray system 1 to the information system 8 in a simple manner offers wide-ranging possibilities for documentation and quality assurance.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray system comprising:
    an x-ray apparatus operable for conducting an x-ray examination involving setting of at least one operating parameter of the x-ray apparatus;
    a plurality of different types of auxiliary equipment respectively selectably usable in combination with said x-ray apparatus for conducting said examination; and
    a control system in communication with said x-ray apparatus comprising a data input device that identifies one of said types of auxiliary equipment selected for said examination, a data storage device containing data defining respective optimal settings of said at least one parameter for each of said types of auxiliary equipment when said x-ray apparatus is used in combination with each of said types of auxiliary equipment, and an adjustment device in communication with the x-ray apparatus that automatically sets said at least one parameter of said x-ray apparatus dependent on the identified auxiliary equipment for said examination.

2. An x-ray system as claimed in claim 1 comprising a medical information system in communication with said control system, said control system providing said medical information system with data identifying said examination and the auxiliary equipment used for said examination.

3. An x-ray system as claimed in claim 1 wherein said data input device is a barcode scanner, and wherein said auxiliary equipment carries a barcode recognizable by said barcode scanner.

4. An x-ray system as claimed in claim 1 wherein said auxiliary equipment is a guide wire.

5. An x-ray system as claimed in claim 1 wherein said auxiliary equipment is a catheter.

6. An x-ray system as claimed in claim 1 wherein said auxiliary equipment is a contrast agent injector.

7. An x-ray system as claimed in claim 1 wherein said data storage device contains, as said at least one parameter, a plurality of settings that influence an x-ray spectrum of said x-ray apparatus.

8. An x-ray system as claimed in claim 1 wherein said data storage device contains, as said at least one parameter, a plurality of settings that influence a focus of an x-ray image produced by said x-ray apparatus.

9. An x-ray system as claimed in claim 1 wherein said data storage device contains, as said at least one parameter, a plurality of settings that influence an image processing filter of said x-ray apparatus.

* * * * *